United States Patent [19]

Shih

[11] Patent Number: 5,156,970
[45] Date of Patent: Oct. 20, 1992

[54] METHODS OF VIRAL PROPAGATION AND GENE EXPRESSION

[75] Inventor: Chiaho Shih, Paoli, Pa.

[73] Assignee: Trustees of the University of Pennsylvania, Philadelphia, Pa.

[21] Appl. No.: 228,600

[22] Filed: Aug. 4, 1988

[51] Int. Cl.$^5$ .................. C12N 5/00; C12N 15/00
[52] U.S. Cl. .................. 435/240.2; 435/172.3
[58] Field of Search .................. 435/240.2

[56] References Cited

PUBLICATIONS

DuBois et al DNAS 77(8):4549. 1980.
Sureau et al. Cell 47:37. 1986.
Yaginuma et al., *Proc. Natl. Acad. Sci. USA*, 84: 2678–2682 (1987).
Chang et al., *EMBO J.*, 6(3): 675–680 (1987).
Tsurimoto et al., *Proc. Natl. Acad. Sci. USA*, 84: 444–448 (1987).
Sells et al., *Proc. Acad. Sci. USA*, 84: 1005–1009 (1987).
Zelent et al., *J. of Virol.*, 61: 2921–2923 (1987).
Seifer et al., 1987 *Meetings on Hepatitis B Viruses*, p. 11, Cold Spring Harbor Laboratory (N.Y. 1987).
Pourcel et al., 1987 *Meetings on Hepatitis B Viruses*, p. 92, Cold Spring Harbor Laboratory (New York, 1987).
*Recent Results in Cancer Research-Special Topics in Carcinogenesis*, E. Grundamann, ed., 44: 103–114 (1974).

*Primary Examiner*—Elizabeth C. Weimar
*Assistant Examiner*—Suzanne Ziska
*Attorney, Agent, or Firm*—Woodcock Washburn Kurtz Mackiewicz & Norris

[57] ABSTRACT

Novel methods for stable in vitro propagation of human hepatitis virus using non-human hepatocytes are disclosed. Also discussed are novel systems for efficient expression and secretion of foreign genes employing particular rat hepatoma cells.

5 Claims, No Drawings

METHODS OF VIRAL PROPAGATION AND GENE EXPRESSION

REFERENCE TO GOVERNMENT GRANT

This work was supported in part by a research grant from the National Institutes of Health, grant number NIHR01 CA43835. The United States Government has certain rights in this invention.

BACKGROUND OF THE INVENTION

Hepatitis type B virus (HBV) is a pathogen of considerable interest to the medical community. An etiological agent in acute and chronic hepatitis and liver cirrhosis, this virus has also been linked to hepatocellular carcinoma. In certain areas of the world such as Central Africa and East Asia, as many as ten percent of the population carry HBV, and a large percentage of these individuals die from its effects.

Investigations into the replication, expression and other aspects of the life cycle of HBV in an effort to develop antiviral drugs and immunological agents, have been hampered, in part, by the elusiveness of a suitable stable cell line for in vitro propagation of infectious virus. Numerous investigators, such as Yaginuma et al., Proc. Natl. Acad. Sci. USA, 84: 2678-2682 (1987) and Chang et al., EMBO J., 6(3): 675-680 (1987) tried, but were unable, to establish stable culture systems using relatively differentiated human hepatocellular carcinoma cell line HuH-7. A few select investigators did eventually report success using the relatively differentiated human hepatoma cell lines Huh6-c15 and HepG2. See Tsurimoto et al., Proc. Natl. Acad. Sci. USA, 84: 444-448 (1987), Sureau et al., Cell, 47: 37-47 (1986) and Sells et al., Proc. Acad. Sci. USA, 84: 1005-1009 (1987). To date, however, no successful efforts have been reported in which a nonhuman cell line of any differentiated state has been stably transfected in vitro with human HBV genome. See Zelent et al., J. of Virol., 61: 2921-2923 (1987) and Seifer et al., "1987 Meetings on Hepatitis B Viruses," pp. 11, Cold Spring Harbor Laboratory (N.Y., 1987). Additional stable in vitro systems, including nonhuman systems, are needed. Cell lines capable of efficient expression and secretion of the gene products of hepatotropic viruses such as human HBV would also be useful. The present invention is directed to these ends.

SUMMARY OF THE INVENTION

The present invention pertains to a non-human hepatocyte transfected with at least one human hepatitis virus genome, said hepatocyte being capable of stable in vitro propagation of said virus.

The present invention also includes a rat hepatoma cell selected from the group consisting of Q7-P and Q7 wherein said rat hepatoma cell comprises at least one gene.

The cells of the invention provide a efficient system for the propagation of infectious human hepatitis virus, the expression of these and other foreign genes, and the secretion of the resultant gene products into the extracellular environment. The cells and/or gene products thereof can be employed in many uses, including the screening of drug candidates, the detection of antibodies and the production o vaccines.

DETAILED DESCRIPTION OF THE INVENTION

The present invention pertains to non-human hepatocytes transfected with at least one human hepatitis virus genome, the hepatocytes being capable of stable in vitro propagation of the hepatitis virus. The non-human hepatocytes of the subject invention provide an efficient system for the propagation of infectious virus.

As used herein, the phrase "in vitro viral propagation" or variations thereof shall be taken to mean the replicative production in cell culture of fully intact infectious human hepatitis virus. The invention provides, for the first time, a stable non-human in vitro system for carrying out such human hepatoviral propagation. By "stable," it is meant a system that is able to maintain viral propagation for at least one month. Preferred is the maintenance of propagation for at least six months. More preferred is maintenance of propagation for at least one year. Most preferred is maintenance for at least five years.

The non-human hepatocyte utilized in this aspect of the invention may be selected from immortalized or non-immortalized liver cells. As used throughout this specification, unless otherwise noted, the term "hepatocyte" shall be taken to encompass both of these types of cells. Suitable non-immortalized cells are primary culture cells, that is, early generation cells derived from in vivo tissue. Suitable immortalized cells include any type of hepatoma cells (e.g. hepatoblastoma, hepatocellular carcinoma, etc.). Preferable hepatocyte cells include rodent hepatocyte cells (including rat, mouse, woodchuck, ground squirrel, tree squirrel, etc.), particularly rat hepatocyte cells. More preferable hepatocyte cells are rodent hepatoma cells, particularly rat hepatoma cells, and most particularly N-2-fluorenylphthalamic acid (N-2-FPA) induced rat hepatoma cells such as Q7-P and Q7. Cells Q7-P were originally derived from a N-2FPA induced rat hepatoma, designated 7777, described in Morris, H. P. and Meranze D. R.,"Recent Results in Cancer Research," Grundmann, E., ed., Vol. 44, pp. 103-114 (Springer-Verlag, N.Y., 1974). Other N-2-FPA induced rat hepatoma cells are also described in that publication. Q7 cells are variant progeny derived from the Q7-P parental cell line. A sample of each of the Q7-P and Q7 cell lines has been deposited with the American Type Culture Collection (ATCC), 12301 Parklawn Drive, Rockville, Maryland 20852. The deposited Q7-P cell line bears ATCC deposit accession number CRL 9770. The Q7 cell line deposit has been assigned ATCC deposit accession number 9769. Most preferably, the invention is carried out with the deposited Q7-P cell line and/or the deposited Q7 cell line, particularly the deposited Q7 cell line. Included herein in any use of the phrases "deposited Q7" and "deposited Q7-P" or variations thereof are not only the deposited cells, but any and all progeny thereof.

In accordance with the invention, the non-human hepatocyte cells are transfected with a human hepatitis virus genome. As used herein, the term transfection denotes the introduction of foreign genetic material, such as, for example, a viral genome, into cells. Conventional methods such as calcium phosphate treatment and electroporation can be employed. Calcium phosphate treatment is preferred, and is described in detail in Shih et al., Cell, 29: 161-169 (1982). Other gene transfer techniques are set forth in "Gene Transfer," R. Kuchelapati, ed. (Plenum Press, N.Y., 1986).

The human hepatitis virus employed may be human hepatitis type A virus, human hepatitis type B virus, and/or human hepatitis type non-A/non-B virus. Additionally, if desired, the hepatitis type B transfected cells can be further transfected with human delta virus, a viral parasite to HBV. As used herein, the term "virus" denotes both wild-type and suitable mutant strains. Such suitable mutant strains and methods of creating the same, will be readily apparent to those skilled in the art.

In a most preferred embodiment of this aspect of the invention, the rat hepatoma cell Q7, ATCC deposit accession number CRL 9769, is transfected with the human hepatitis type B virus genome. A resulting transfected cell line, designated Q7HBV-21, is on deposit with the ATCC, bearing accession number CRL 9768. Included in any use of the phrase "deposited Q7HBV-21" or variations thereof are not only the deposited cells, but any and all progeny thereof.

The non-human hepatocytes thus transfected can be put to a variety of scientifically and commercially important uses, as described in greater detail below.

The present invention is further directed to rat hepatoma cells selected from the group consisting of Q7-P and Q7 wherein the rat hepatoma cell comprises at least one foreign gene. The rat hepatoma cells of the subject invention provide an efficient system for the expression of such genes and secretion of the gene products.

The rat hepatoma cells utilized in this aspect of the invention are selected from the group of cells consisting of Q7-P and Q7. Cells Q7-P and Q7 are described above. Preferably, the Q7-P and Q7 cells employed are the deposited cell lines, as previously described. Most preferably the invention utilizes the deposited Q7 cell line.

The genes used in the present invention can be any compatible gene, as those skilled in the art would recognize. As employed herein, the term "gene denotes both a full length as well as an expressible portion of a gene, and includes both wildtype and mutants. Suitable genes, gene portions and mutations, and methods of obtaining the same, will be readily apparent to those skilled in the art. The ter "foreign" denotes that the gene is obtained from a source external to the Q7 or Q7-P rat hepatoma recipient cells.

Preferably, the gene is a liver-specific foreign gene. The phrase "liver-specific gene," as used herein, denotes genes which code for gene products found in wild-type hepatocyte cells. Such genes include not only genes from a hepatocyte cellular genome, but also genes from hepatotropic viruses present in other species. Suitable cellular genes include, among other things, the genes of tissue plasminogen activator (TPA), fibrinogen, transferin, $\alpha$1-antitrypsin, $\alpha$1-antichymotrypsin, complement C3 and complement C4. Suitable hepatotropic viral genes include, but are not limited to, genes from the human hepatitis type B virus, the human delta virus, the human hepatitis type A virus, and the human hepatitis type non-A/non-B virus. Such human hepatitis type B genes include the surface antigen gene family, the core (or e) antigen gene, the polymerase gene and the so-called X gene. For a general overview of liver-specific genes, see "Meeting on Regulation of Liver Gene Expression", Cold Spring Harbor Laboratory (N.Y., Apr. 29 through May 3, 1987).

In a most preferred embodiment of this aspect of the invention, the Q7 rat hepatoma cell of ATCC deposit accession number CRL 9769 is transfected with the entire genomic material of the human hepatitis type B virus. As described earlier, this cell line, designated Q7HBV-21, has been deposited with the ATCC, under accession number CRL 9768.

Preparation of the foreign genes for introduction into the Q7 or Q7-P cells can be carried out using conventional methods. Introduction of the foreign genes into the rat hepatoma cells can take place in a variety of ways, as will be apparent to those skilled in the art, such as by calcium phosphate transfection procedures. The gene thus introduced may then be incorporated into the genome of the recipient rat hepatoma cell, or remain as an extrachromosomal segment of genetic material, as the case may be.

Once properly introduced into the rat hepatoma cells, the gene products can be expressed and efficiently secreted by the cells into the extracellular medium, where they can be separated, if desired, and employed for various uses, as described in detail below.

For suitable genetic engineering techniques for the preparation, introduction and expression of the foreign genes, see Maniatis, J., et al., "Molecular Cloning—A Laboratory Manual," Cold Spring Harbor Laboratory (1982); Shih et al. Proc. Natl. Acad. Sci, 76: 5714–5718 (1979); Shih et al., Cell, : 161-169 (1982); "Gene Transfer," R Kuchelapati, ed. (Plenum Press, N.Y. 1986); and "Meeting on Regulation of Liver Gene Expression," Cold Spring Harbor Laboratory (N.Y., April 29 –May 3, 1987).

The present invention has numerous uses, as will be evident to those skilled in the art. With respect to hepatocytes stably transfected with human hepatitis type B virus for example, the present invention provides a system for studying the replication, expression and other aspects of the life cycle of this poorly understood pathogenic virus. Such studies will likely prove highly beneficial in the development of effective antiviral drugs, immunological agents, and clinical detection assays for the virus.

In addition, hepatocyte cells of the subject invention transfected with hepatitis virus may be employed in to determine the efficacy of drug candidates for the treatment of human hepatitis virus infections. The process is be carried out by (i) applying anti-hepatitis virus drug candidates at various dilutions or combinations to at least one cell; and (ii) screening for the diminution (including cessation) of viral replication. Generally, the drug candidates are applied at lower amounts initially, and increased until the desired effect is observed. During the application step, the cells are generally in culture. Screening can be accomplished using conventional techniques such as dot blot or Southern blot analysis, as described in Maniatis, T., et al., "Molecular Cloning—A Laboratory Manual," Cold Spring Harbor Laboratory (N.Y., 1982). The preferable screening technique would be dot blot analysis. Cellular toxicity induced by anti-viral drug applications could additionally be monitored. Such monitoring can be carried out visually, using phase contrast microscopy.

Moreover, hepatocytes or hepatomas transfected with at least one human hepatitis virus gene, or preferably, the entire viral genome, in accordance with the present invention may be employed to produce antigen-containing medium. The medium or the antigens separated therefrom in turn may be used in the detection of antibodies against hepatitis virus in the serum of a patient, thus providing a new and useful important clinical diagnosis and prognosis tool. The detection method involves i) contacting the serum of a patient with antigens produced by the aforementioned cells, and (ii) screening for antigen-antibody interactions. The efficient secretory ability of the cells utilized in the present invention results in the accumulation of such antigenic materials in the culture medium. If desired, the antigens may be separated from the medium using conventional means. As one skilled in the art would recognize, separation and recovery of these antigenic materials can be expedited by the use of serum free medium or low serum medium. Screening can be carried out using conventional methods known to those skilled in the art such as enzyme immunoassay and radiommunoassay.

Further, the cells transfected with at least one human hepatitis gene, or preferably the entire genome may be employed in the production of vaccines, as will be evident to those skilled in the art. One method of vaccine preparation currently employed is to collect HBV specific antigens from the plasma of HBV asymptomatic carriers. The possibility of contamination from the AIDS virus or any other infective adventitious agents as well as the scarcity of acceptable vaccine plasma donors has made this method of vaccine preparation considerably less desirable. Although yeast produced vaccine of HBV specific surface antigen is currently available, its immunological performance is relatively weak, partly due to the absence of some important epitopes. The observation of Dane-like particles in the conditioned medium of Q7HBV-21 indicates the presence of a complete spectrum of HBV specific gene products, including the major surface antigens. To employ as a vaccine, the infectivity of the virus particles (the Dane-like particles) produced by a transfected hepatocyte cell of the present invention can be attenuated or inactivated by, for example, ultraviolet light exposure or treatment with pepsin, urea or formaldehyde. The use of mammalian cells in the present invention and the concomitant ability of these cells to carry out antigenically important cellular processing such as glycosylation, makes this system particularly useful in and vaccine production. The attenuated inactivated viral particles produced from cells such as Q7HBV-21 should induce a much stronger immune response than any presently employed vaccines.

These and other uses of the invention will be readily apparent to those skilled in the art.

Deposit of Biological Materials

The preferred cell lines for use in the subject invention, Q7-P and Q7, were deposited on Jul. 26, 1988 with the American Type Culture Collection (ATCC), 12301 Parklawn Drive, Rockville, Maryland 20852. Cell line Q7-P has been assigned ATCC deposit accession number CRL 9770. Cell line Q7 bears ATCC deposit accession number CRL 9769. The preferred cells of the invention, Q7HBV-21, which comprise rat hepatoma cells Q7 ATCC deposit accession number CRL 9769 transfected with human hepatitis type B virus, was also deposited on Jul. 26, 1988 with the ATCC, and has been assigned ATCC deposit accession number CRL9768.

EXAMPLES

The invention is further described in the following Examples. These Examples are intended to be exemplary, but not limiting, of the present invention.

Materials and Methods

1. Construction of Donor DNA:

A pcp10 HBV-containing plasmid as described in Dubois et al., Proc. Natl Acad. Sci., 77:4549–4553 (1980), was obtained, and was linearized with EcoRI. The resulting 3.1 kb HBV DNA fragment was electroeluted from gel and ligated with EcoRI cut pSV232ANeo vector, described in Kadesch et al., Mol. Cell Biol. :2593-2601 (1986). This ligated DNA mixture was transformed into TGI $E.$ $coli.$ The pSV232ANeo-HBV monomer was screened with EcoRI digestion of mini-prep DNA. A partial digestion of the PSV232ANeo-HBV monomer DNA with EcoRI was carried out. The linearized 9.3 kb band was then electroeluted from gel and ligated to an EcoRI-cleaved 3.1 kb HBV DNA insert. Transformed colonies of head-to-tail tandem dimer, designated as pSV232ANeo(HBV)$_2$, were screened with XhoI, which gave rise to a 3.1 kb HBV DNA insert.

2. Transfection and Cell Culture:

The rat hepatoma cell line Q7 was used for these experiments. Q7 is on deposit with the American Type Culture Collection (ATCC), 12301 Parklawn Drive, Rockville, Maryland 20852, bearing Accession Number CRL 9769. Q7 was maintained in 5-10% fetal bovine serum in DMEM (Dulbecco's Modified Eagle's Medium), at 37° C. in the presence of 5.5% $CO_2$. Calcium phosphate transfection procedure was followed as detailed in Shih et al., Cell, 29:161-169 (1982). Briefly, $7 \times 10^5$ Q7 cells per 10 cm dish were transfected with 5-10μg pSV232ANeo(HBV)2 DNA plus 20μg of human genomic DNA as carrier. Donor DNA was removed 4 hrs later after transfection. Neo$^r$ colonies were isolated four weeks later. G418 (Geneticin, purchased from Gibco, Inc.) used at the final concentration of 1.3 mg/mc and was removed from medium three months after transfection.

3. Detection of eAo and Surface Ag:

Conditioned media from Neo$^r$ Q7 cell lines were assayed according to the conventional procedures recommended by the vendors, Abbott Laboratories, Inc., in their brochure for Auszyme TM Monoclonal Enzyme Immunoassay kit for the detection of hepatitis B Surface Antigen (1987). See also generally the procedures set forth in Ling, C.N. "Hepatitis B," Millman, I., Eisenstein, T.K., Blumberg, B.S. eds., pgs. 95–104 (Plenum Press, N.Y., 1984).

4. Fractionation cf Extracellular HBV Particles:

Eighty ml of conditioned media from each sample were precleared at 2500 rpm for 10 minutes at room temperature. Twenty-seven ml of cell-free media were pelleted through an 11 ml 20% sucrose cushion in TNE buffer (50 mm NaCl; 20 mm Tris-HCl) in an SW 28 rotor at 25 krpm for 16 hrs at 4° C. Each pellet was resuspended in 0.5 ml TNE buffer and loaded onto a 20-50% cesium chloride isophysic gradient in an SW 50.1 rotor. After centrifugation at 35 krpm at 4.C for 16 hrs, about 0.3 ml per fraction were collected from the bottom of the tube. The buoyant density of each fraction was measured occasionally with a refractometer.

5. Electron Microscopy:

Putative Dane particle containing fractions from a cesium chloride gradient were pooled together and changed with TNE buffer via a Centricon 10 concentrator (Amicon). From the starting material of 80 ml conditioned medium, approximately 50-100 microliter of final volume was expected. About 10 microliter volume was applied to each Formvar-coated grid, followed by washing with 6 drops of 0.1 M ammonium acetate buffer and stained with freshly filtered 1% uranyl acetate. JEOL 40000EX electron microscope was used for photography.

6. DNA and RNA Analysis:

Genomic DNA was prepared using the procedures detailed in Shih et al., Proc. Natl. Acad. Sci., 76:5714–5718 (1979). Hirt extraction protocol was adopted from Hirt, J. Mol. Biol. 26:365–369 (1967). Preparation of RNA was carried out according to Chirgwin et al., Biochemistry, 18:5294–5299 (1979). Southern and Northern blot analyses were conducted using standard procedures well known in the art. See Maniatis, T., et al., "Molecular Cloning—A Laboratory Manual," Cold Spring Harbor Laboratory (N.Y., 1982).

7. Polymerase Assay:

Core particle containing fractions from cesium chloride gradient was changed with EB buffer (20 mM-Tris HCL, pH 7.4; 7 mM $MgSO_4$; 50 mM Nacl) by a Centricon 10 concentrator (Amicon). From the starting material of 80 ml conditioned medium, approximately 50 to 100 microliter of final volume was obtained. About 30 $\lambda$ volume was used in each assay. Briefly, 30 $\lambda$ core particles in EB buffer was mixed with 0.5 $\lambda$. bovine serum albumin (BSA) (10 mg/ml), 5 $\lambda$ sucrose (2.0 M) and 2.5 p-nitrophenyl-40 (NP40) (10%). To this mixture, each of d ATP (0.5 mM), TTP (0.5 mM), dGTP (0.5 mM) and 2 $\lambda^{32}P$-dCTP (3000 ci/mmol) were added and incubated at 37° C. for 1 hr. The reaction was stopped by adding 1 $\lambda$ SDS (10%) and 1 $\lambda$ proteinase K stock (5 mg/ml). After incubation at 37° C. for 2 hrs, loading dye containing EDTA, SDS and glycerol was added to each sample and analyzed on 1.5% agarose gel (containing 0.1% SDS). Electrophoresis was conducted at 40 volts for 12 hrs. Ethidium bromide stained gel was then fixed in methanol for 1 hr, followed by extensive washing with 3–4 changes of distilled water. Gels were dried under vacuum at 80.C for 1 hr, and exposed to Kodak XAR-5 film for autoradiogram.

Results

Approximately one dozen Q7 rat hepatoma cell lines were identified a stably established and able to support human hepatitis type B virus production, as characterized by the following criteria:

1) high levels of accumulation of secreted core/e Ag were identified in the conditioned media as measured by EIA assay;

2) high levels of accumulation of secreted surface antigen were identified in the conditioned medium as measured by EIA assay and electron microscopy. Both 22 nm spherical and filamentous-shaped forms of surface antigen are observed;

3) characteristic DNA replication intermediates of hepatitis type B virus, including relaxed circle and single stranded linear forms, was clearly identified by Southern blot analysis;

4) characteristic hepatitis type B virus specific transcripts including 3.5 kb pregenomic RNA, 2.5 kb and 2.1 kb surface antigen specific RNA were detected by Northern blot analysis;

5) extracellular particles enriched from a cesium chloride density gradient exhibited hepatitis type B virus-specific endogenous polymerase activity; and 6) electron microscopic examination identified Dane-like particles with a double-shell, concentric shape and an average diameter near 42 mm, and a buoyant density near 1.25 $g/cm^3$.

What is claimed is:

1. A rat hepatoma wherein said rat hepatoma is transfected with at least two human hepatitis B virus genomes and capable of stable in vitro propagation of said virus.

2. A rat hepatoma according to claim 1, wherein said rat hepatoma is Q7 rat hepatoma, ATCC deposit accession number CRL 9769.

3. A non-human hepatocyte cell line which Q7HBV-21, ATCC deposit accession number CRL 9768.

4. A rat hepatoma cell which is Q7HBV-21, ATCC deposit accession number 9768transfected with at least one heterologous gene.

5. A rate hepatoma cell according to claim 4, wherein said heterologous gene is a human tissue plasminogen activator gene.

* * * * *

UNITED STATES PATENT AND TRADEMARK OFFICE
CERTIFICATE OF CORRECTION

PATENT NO. : 5,156,970

DATED : October 20, 1992

INVENTOR(S) : Chiaho Shih

Page 1 of 2

It is certified that error appears in the above-identified patent and that said Letters Patent is hereby corrected as shown below:

In column 1, line 61: "provide a efficient" should read "provide an efficient"

In column 1, line 68: "production o vaccines." should read "production of vaccines."

In column 3, line 37: "the term "gene denotes" should read "the term "gene" denotes"

In column 3, line 42: "The ter" should read "The term"

In column 4, line 24: "Shih et al., Cell,:" should read "Shih et al., Cell, 29:"

In column 6, line 7: "Cell Biol.:" should read "Cell Biol., 6:"

In column 6, line 31: ...transfection. Neor... An italicized superscript "r" should be inserted in place of the "r" in "Neor" and should read "Neo$^r$"

In column 6, line 46: "Fractionation cf" should read "Fractionation of"

In column 6, line 55: "35 krpm at 4.C" should read "35 krpm at 4°C"

In column 7, line 37: "at 80.C" should read "at 80°C"

UNITED STATES PATENT AND TRADEMARK OFFICE
CERTIFICATE OF CORRECTION

PATENT NO. : 5,156,970
DATED : October 20, 1992
INVENTOR(S) : Chiaho Shih

It is certified that error appears in the above-indentified patent and that said Letters Patent is hereby corrected as shown below:

In column 7, line 42: "identified a stably" should read "identified as stably"

In claim 4, Column 8, line 37: "9768transfected" should read "9768, transfected"

In claim 5, Column 8, line 39: "A rate" should read "A rat"

Signed and Sealed this

Twenty-eighth Day of December, 1993

Attest:

BRUCE LEHMAN

*Attesting Officer*  *Commissioner of Patents and Trademarks*